United States Patent
Syvret et al.

(10) Patent No.: US 6,524,990 B2
(45) Date of Patent: Feb. 25, 2003

(54) ACTIVE FLUORIDE CATALYSTS FOR FLUORINATION REACTIONS

(75) Inventors: Robert George Syvret, Allentown, PA (US); Philip Bruce Henderson, Allentown, PA (US); Donald Elson Fowler, Coopersburg, PA (US); Beth Ann Campion, Allentown, PA (US); Frederick Carl Wilheim, Zionsville, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/783,900

(22) Filed: Feb. 15, 2001

(65) Prior Publication Data

US 2002/0147364 A1 Oct. 10, 2002

(51) Int. Cl.$^7$ .......................... B01J 27/06; B01J 27/138; B01J 27/135; B01J 27/132
(52) U.S. Cl. ...................... 502/224; 502/226; 502/227; 502/228; 502/229; 502/231
(58) Field of Search ................................ 502/224, 226, 502/229, 227, 231, 228

(56) References Cited

U.S. PATENT DOCUMENTS

| | | | |
|---|---|---|---|
| 2,689,254 A | | 9/1954 | Cady et al. ............... 260/453 |
| 3,394,163 A | | 7/1968 | Kroon ....................... 260/453 |
| 3,717,586 A | * | 2/1973 | Suggitt et al. ............. 252/439 |
| 3,898,297 A | | 8/1975 | Sampson et al. .......... 260/668 |
| 4,088,705 A | * | 5/1978 | Pieters et al. ............. 260/653.7 |
| 4,499,024 A | | 2/1985 | Fifolt ....................... 260/453 |
| 4,798,818 A | * | 1/1989 | Baizer et al. ............. 502/228 |
| 5,494,876 A | * | 2/1996 | Tsuji et al. ............... 502/224 |
| 5,849,658 A | * | 12/1998 | Shibanuma et al. ...... 502/228 |
| 5,981,813 A | | 11/1999 | Cuzzato et al. ........... 570/166 |

FOREIGN PATENT DOCUMENTS

| | | | |
|---|---|---|---|
| EP | 0879808 | 11/1998 | ........... C07B/39/00 |

OTHER PUBLICATIONS

Frederick A. Hohorst and Jean'ne M. Shreeve, *Journal of the American Chemical Society*, vol. 89, (1967), pp. 1809–1810 Sep. 1966.
Ronald L. Cauble and George H. Cady, *Journal of the American Chemical Society*, vol. 89 (1967), p. 1962 Sep. 1966.
Max Lustig, et al., *Journal of the American Chemical Society*, vol. 89 (1967), pp. 2841–2843 Nov. 1966.
Michael J. Fifolt, et al., *Journal of Organic Chemistry*, vol. 50 (1985), pp. 4576–4582 Aug. 1984.
R. Craig Kennedy and George H. Cady, *Journal of Fluorine Chemistry*, vol. 3, (1973/74), pp. 41–54 Nov. 1972.

* cited by examiner

*Primary Examiner*—Mark L. Bell
*Assistant Examiner*—Patricia L. Hailey
(74) *Attorney, Agent, or Firm*—Mary E. Bongiorno

(57) ABSTRACT

Active fluoride catalysts that are useful in producing electrophilic fluorination agents; especially useful in producing BDM from the reaction of fluorine with carbon dioxide and FTM from the reaction of fluorine with carbonyl fluoride. The fluoride catalyst comprises a mixture of two or more fluorides selected from a transition metal fluoride, an alkali metal fluoride and/or an alkaline earth metal fluoride. Alternately, the fluoride catalyst is one or more fluorides, such as alkali metal fluorides, alkaline earth metal fluorides, and/or transition metal fluorides, deposited on an inert support.

21 Claims, No Drawings

ACTIVE FLUORIDE CATALYSTS FOR FLUORINATION REACTIONS

BACKGROUND OF THE INVENTION

There is a need in the industry for scaleable processes that are capable of generating electrophilic fluorination ($F^+$) agents with sufficient $F^+$ character, or alternatively, $F^+$ power, to affect electrophilic fluorination reactions of a wide variety of organic substrates with high selectivity, and are also safe and economical to produce and use.

Examples of $F^+$ agents which possess sufficient $F^+$ power and selectivity in fluorination reactions with organic substrates include bis(fluoroxy)difluoromethane (BDM) and fluoroxytrifluoromethane (FTM.) BDM and FTM can be produced in a cesium fluoride (CsF)-catalyzed reaction between fluorine and carbon dioxide or fluorine and carbonyl fluoride, as shown in the reaction schemes below.

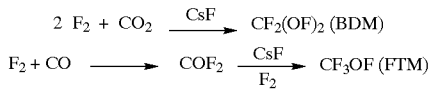

The preparation and handling of the CsF catalyst is critical to its effectiveness as a catalyst. The CsF must be rigorously dried and totally free of water and hydrogen fluoride. Even a minimum exposure of the bulk catalyst bed to either water or hydrogen fluoride can result in an immediate and irreversible loss of catalytic activity.

One of the major problems in using a CsF catalyst is preparing CsF in an anhydrous condition, and subsequently loading a vessel with the dry material while preserving the anhydrous condition. A known method for preparing the CsF catalyst is to melt CsF at 800° C. and then allow the molten material to cool and solidify in a moisture-free glovebox. The solidified material is then finely ground using a combination of mortar/pestle and electric grinder. The catalyst material so prepared is transferred, inside the dry atmosphere of a glovebox, to the reactor.

A problem with the above method of catalyst preparation is the fine powder form of the activated catalyst material. When loaded into the catalyst vessel, the fine powder can create an unacceptable pressure drop across the vessel. This becomes especially problematic at the high gas flow rates that are required in large scale BDM and FTM technologies. Another problem arises when performing the above described catalyst preparation procedure on the scale required for commercial scale use. Commercial scale catalyst vessels can be too large and unwieldy to be handled in a conventional drybox. A further problem with the above described catalysts is the potential for channeling which compromises efficiency of the catalyst bed.

Other fluorides, such as potassium fluoride and sodium fluoride, have been shown to catalyze specific fluorination reactions.

Examples of processes for producing BDM and FTM using fluoride catalysts are described in the following publications:

Frederick A. Hohorst and Jean'ne M. Shreeve (*Journal of the American Chemical Society*, V.89, (1967), pages 1809–1010,) describe the static fluorination of carbon dioxide with a large (305%) molar excess of fluorine in the presence of a large (18 mmoles) molar excess of cesium fluoride to prepare BDM.

Ronald L. Cauble and George H. Cady (*Journal of the American Chemical Society*, V. 89 (1967), page 1962) describe a preparation of BDM in which carbon dioxide was reacted with nearly 100% excess fluorine in the presence of pulverized CsF as the catalyst.

Max Lustig, et al. (*Journal of the American Chemical Society*, V.89 (1967) pages 2841–2843) describe a low temperature preparation of fluoroxy compounds, including BDM, by catalytic fluorination of carbonyl halides and fluoroalkyl acid fluorides. Finely ground cesium fluoride was used in the examples.

U.S. Pat. No. 3,394,163 (Kroon, 1968) discloses preparation of BDM by treating an alkali metal oxalate with fluorine in the presence of an alkali metal fluoride or an alkaline earth metal fluoride catalyst.

U.S. Pat. No. 4,499,024 (Fifolt, 1985) discloses a continuous reaction for preparing BDM by reacting carbon dioxide and fluorine in the presence of CsF catalyst. The reactants are passed through a reactor, such as a nickel or nickel-lined tube containing particles or powder of cesium fluoride. In the examples, a 4:1 mole ratio of fluorine:carbon dioxide is used.

Michael J. Fifolt, et al. (*Journal of Organic Chemistry*, V.50 (1985) pages 4576–4582) disclose the production of BDM and FTM by the reaction of fluorine with carbon dioxide and carbon monoxide, respectively, using a cesium fluoride catalyst. It is reported that preparation of cesium fluoride by fusion and subsequent grinding under anhydrous conditions is critical for the reaction to occur.

U.S. Pat. No. 2,689,254 (Cady and Kellogg, 1954) discloses a process for preparing FTM by reacting carbon monoxide and fluorine in the presence of a catalyst comprising a copper ribbon coated with silver fluoride.

R. Craig Kennedy and George H. Cady (*Journal of Fluorine Chemistry*, V.3 (1973/74), pages 41–54,) report on the use of several fluoride catalysts, such as sodium fluoride, ammonium fluoride, and barium fluoride, in the preparation of FTM. Except for the fluorides prepared in the reactor, each catalyst was ground to a fine powder before it was added to the reactor.

The need remains for an effective catalyst that can be used in large scale fluorination processes; for example, a catalyst that will not create a large pressure drop across a vessel used in large scale production of BDM or FTM.

BRIEF SUMMARY OF THE INVENTION

This invention is directed to new active fluoride catalysts that are useful in producing electrophilic fluorination agents. The new active fluoride catalysts are especially useful in producing BDM from the reaction of fluorine with carbon dioxide and FTM from the reaction of fluorine with carbonyl fluoride. The fluoride catalyst comprises a mixture of two or more fluorides selected from a transition metal fluoride, an alkali metal fluoride and an alkaline earth metal fluoride. Alternately, the fluoride catalyst is one or more fluorides, such as alkali metal fluorides, alkaline earth metal fluorides, and/or transition metal fluorides, deposited on an inert support, such as a zirconium oxide ($ZrO_2$) support. The catalysts of this invention are in the form of particles or pellets such that the surface area is preferably at least about 0.1 $m^2$ per gram.

In an embodiment of this invention, the active fluoride catalysts are formed by depositing an aqueous mixture of one or more of an alkali metal salt, an alkaline metal salt, and/or a transition metal salt on an inert support, heating the supported salts to evaporate the water, thoroughly drying the supported salts under dry nitrogen, and activating the salts by passing fluorine or fluorine-containing gas over the supported material to convert the salt to a fluoride.

In another embodiment of this invention, the active fluoride catalysts are formed by mixing together, in an aqueous medium, a transition metal salt, preferably a fluoride, and one or more of an alkali metal salt, alkaline earth metal salt, and/or another transition metal salt, heating the mixture to evaporate the water, extruding the dried mixture, breaking the extrudate into particles or pellets, thoroughly drying the particles under dry nitrogen, and activating the salts by passing fluorine or fluorine-containing gas over the supported material to convert the salt to a fluoride.

In another embodiment of this invention the above catalysts are used in fluorination reactions in which BDM is formed from the reaction of fluorine and carbon dioxide or FTM is formed from the reaction of fluorine and carbonyl fluoride.

In another embodiment of this invention, the above catalysts are formed in situ prior to reacting fluorine and carbon dioxide to form BDM or fluorine and carbonyl fluoride to form FTM.

The fluorination catalysts prepared by the method of this invention provide the following advantages compared to known catalysts:

- eliminates the need for large scale melting and grinding equipment in making the catalyst;
- the size of the catalyst particles prevents high pressure gradients in large scale fluorination reactors;
- the catalysts can be made and activated in situ prior to using them in a fluorination reaction;
- use of the catalysts in situ reduces or eliminates the problems associated with handling hygroscopic fluorides under anhydrous conditions;
- little or no fluorine or byproducts are produced in the fluorination reaction; and
- less catalyst is needed for fluorination reactions.

DETAILED DESCRIPTION OF THE INVENTION

The active fluoride catalysts of this invention can be prepared by depositing, on an inert support, an aqueous mixture of one or more salts of an alkali metal, an alkaline earth metal, and/or a transition metal. Examples of appropriate salts are carbonates, bicarbonates, oxides, halides, sulfates, phosphates, nitrates, or hydroxides. Examples of alkali metal, alkaline earth metal, and transition metals are cerium, cobalt, cesium, potassium, sodium, rubidium, lithium, beryllium, magnesium, calcium, barium, and strontium. Examples of inert supports are zirconia, alumina, titania, magnesia, clays, aluminosilicates, and silica.

The wet supported material is heated to a temperature of about 100° C. to evaporate most of the water. It is then thoroughly dried by heating it up to 800° C. under a flow of a dry inert gas, preferably dry nitrogen. In some cases, heating to a temperature that results in decomposition of the salt to an oxide, during drying, is preferred.

Alternately, the catalysts of this invention can be prepared by mixing a transition metal salt, preferably a fluoride such as cerium fluoride, with one or more salts of an alkali metal, an alkaline earth metal, and/or another transition metal. The salt can be any of the salts listed above for the preparation of a supported catalyst. The salt and fluoride are mixed together in an aqueous medium, preferably water, and dried in an oven at a temperature of 100 to 150° C. The mixture can then be extruded using known extruding equipment, to form an extrudate that is typically about ⅛ inch in diameter. The extrudate is thoroughly dried again under an inert gas, preferably nitrogen, at a temperature of at least 100° C. and broken into smaller particles, for example, pelletized, such that the surface area of the particles is preferably at least 0.1 m$^2$/g. The particles are then dried again under nitrogen at a temperature of at least 400° C.

The catalysts of this invention can also be prepared from a mixture of one or more salts of alkali metals, alkaline earth metals, and/or transition metals by a method as described above.

The dried catalytic material are activated by passing fluorine or fluorine-containing gas over the catalytic material to completely convert the salts to fluorides. The fluorine gas can be undiluted fluorine, or fluorine diluted in an inert gas such as helium, neon, argon, krypton, xenon, nitrogen, carbon dioxide, sulfur hexafluoride, tetrafluoromethane, or nitrogen trifluoride. Alternatively, the fluorinating gas can be sulfur tetrafluoride, nitrogen trifluoride, xenon difluoride, krypton difluoride, oxygen difluoride, or dioxygen difluoride.

Activation of the supported catalysts can be carried out at temperatures ranging from −78 to 150° C. Temperatures of −78 to about 300° C. can be used in the activation of the unsupported catalysts. Pressure can range from sub-ambient (vacuum) to super-ambient (up to about 300 psig (2170 kPa)) during activation.

The catalysts of this invention are in a form that provides low back pressure in a fluorination reactor; for example, pellet, extrudate, sphere, tablet, and honeycomb. Pellets or granules having a surface area of at least 0.1 m$^2$/g are preferred. The above fluorination catalysts are useful in the preparation of fluorination agents. They are especially useful in preparing BDM by the reaction of fluorine and carbon dioxide or FTM by the reaction of fluorine with carbonyl fluoride in a continuous process. The catalysts can also be produced in situ prior to introduction of the fluorine and carbon dioxide for the preparation of BDM or fluorine and carbonyl fluoride for preparing FTM.

In the preparation of BDM, a gas flow of fluorine and carbon dioxide can be passed through a catalyst bed containing a catalytic effective amount of catalyst. The molar ratio of carbon dioxide to fluorine can range from 0.5 to 25; preferably 2.5 to 10.

By catalytic effective amount of catalyst is meant an amount which will convert all available fluorine to product. The amount of catalyst that is required depends on the intended flow rate of reactant gases, the catalyst bed pressure used, the ratio of $CO_2$, $F_2$, and other process parameters.

The temperature in the reactor can range from −50 to 100° C., preferably −10 to 50° C., and the pressure can range from 0 to 400 psig (101 to 2859 kPa), preferably 1 to 300 psig (108 to 2170 kPa). Reaction conditions are adjusted so that the product gas contains little or no detectable fluorine or byproducts.

In the preparation of FTM, a gas flow of fluorine and carbonyl fluoride can be passed through a catalyst bed containing a catalytic effective amount of catalyst. The molar ration of carbonyl fluoride to fluorine can range from 1 to 5; preferably 1 to 2.

The temperature in the reactor can range from −50 to 100° C. (preferably −10 to 50° C.) and the pressure can range from 0 to 400 psig (preferably 1 to 300 psig). Reaction conditions are adjusted so that the product gas contains primarily FTM with little or no detectable fluorine, $COF_2$, or byproducts.

If needed, BDM and FTM can be readily separated from other reaction products by known techniques, such as liquefaction.

The invention will be further clarified by consideration of the following examples, which are intended to be purely exemplary of the invention.

EXAMPLE 1

PREPARATION OF LOW SURFACE AREA SUPPORTED CsF CATALYST

Low surface area (less than 0.1 m$^2$/g) ZrO$_2$ spheres were soak-coated with cesium hydroxide (CsOH) and the resulting supported-cesium material was analyzed and shown to contain about 7% by weight cesium. A 52.4 g sample of the supported-Cs material, containing about 26 mmoles Cs, was loaded into a two-ended Whitey bomb fitted with appropriate on/off valves. The bomb was heated to 320° C. and maintained at this temperature for 48 hours with a flow of dry nitrogen (1 slpm) passing through it. After the specified time the bomb was cooled to room temperature and the flow of nitrogen was replaced with a flow of 360 sccm of 0.6% fluorine (10 sccm 20% v/v fluorine/nitrogen (F$_2$/N$_2$) plus 350 sccm N$_2$). The flow of F$_2$ and N$_2$ was continuously adjusted until a final flow condition of 200 sccm of 20% F$_2$/N$_2$ was attained. A total of 34.5 mmoles F$_2$ was added which represents about 33% mol excess.

EXAMPLE 2

PREPARATION OF BDM USING THE SUPPORTED CsF CATALYST

A gas flow consisting of 147 sccm 10% F$_2$/N$_2$ (14.7 sccm F$_2$) and 197.5 sccm CO$_2$ was flowed through the catalyst bed of Example 1 at 25° C. and at a bed pressure of 100 psig. The composition of the product gas exiting the catalyst bed was continuously monitored using an online infrared spectrometer and UV spectrometer. The product gas contained BDM, CO$_2$, and N$_2$, with no F$_2$ detected (UV level was at the detection limit where BDM absorption interferes). From the IR, the BDM/CO$_2$ molar coefficient ratio was 0.31.

EXAMPLE 3

DEMONSTRATION OF CATALYST ACTIVITY AFTER 3 MONTHS AND COMPARISON TO "STANDARD" CsF CATALYST

The supported CsF catalyst bed described in Example 1 was stored under pressurized dry N$_2$ for a period of 3 months. Its activity as a catalyst was then reassessed and also compared to a "standard" melt-activated CsF catalyst bed.

A "standard" melt-activated CsF bed was prepared by packing a 1-inch×11-inch tube with a bed of CsF (activated by melting, cooling in a N$_2$ atmosphere glovebox, and grinding to a very fine powder) that weighed 286 g (1.88 mol CsF). The bed volume was 142 cm$^3$. A gas flow consisting of 200 sccm 10% F$_2$/N$_2$ (20 sccm F$_2$) and 200 sccm CO$_2$ was flowed through this standard catalyst bed at an average temperature of 28.6° C. and at a bed pressure of 100 psig. The composition of the product gas exiting the catalyst bed was continuously monitored using an online infrared spectrometer and UV spectrometer. The composition of the product gas contained BDM, CO$_2$, and N$_2$, with very little F$_2$ detected (UV reading was 0.169, background not subtracted). From the IR, the BDM/CO$_2$ molar coefficient ratio was 0.23.

Following the above experiment, the gas flow was redirected to the supported CsF catalyst bed of Example 1. A gas flow consisting of 200 sccm 10% F$_2$/N$_2$ (20 sccm F$_2$) and 200 sccm CO$_2$ was flowed through the supported CsF catalyst bed at an average temperature of 30.9° C. and at a bed pressure of 100 psig. The product gas exiting the catalyst bed was continuously monitored using an online infrared spectrometer and UV spectrometer. The product gas contained BDM, CO$_2$, and N$_2$, with very little F$_2$ detected (UV reading was 0.141, background not subtracted). From the IR, the BDM/CO$_2$ molar coefficient ratio was 0.41.

The above experiments show that under identical process conditions, the supported CsF catalyst bed of Example 1 was unexpectedly much more active than the "standard" CsF bed, even though the "standard" bed contained about 72 times the amount of CsF as the supported CsF catalyst bed of Example 1; i.e., 286 g of CsF in the "standard" catalyst bed compared to 4.0 g in the catalyst bed of Example 1.

EXAMPLE 4

PREPARATION OF MODERATE SURFACE AREA ZIRCONIA SUPPORTED CsF CATALYST

Moderate surface area (50 m$^2$/g) ZrO$_2$ extruded pellets were coated with cesium carbonate (CS$_2$CO$_3$) and the resulting supported-Cs material contained about 27% by weight Cs. A 422 g sample of the supported-Cs material (≈857 mmoles Cs) was loaded into a two-ended 1-inch o.d. reactor fitted with appropriate on/off valves. The reactor was heated to 250° C. and maintained at this temperature for 68 hours with a flow of dry nitrogen (1 slpm) passing through it. After the specified time the reactor was cooled to room temperature and the flow of nitrogen was replaced with a flow of 120 sccm of 10% F$_2$ (60 sccm 20% v/v F$_2$/N$_2$+60 sccm N$_2$). After 1 hour, the flows were adjusted to achieve a final flow condition of 100 sccm 20% F$_2$/N$_2$ and 20 sccm N$_2$. A total of 840 mmoles F$_2$ was added over a three-day period.

EXAMPLE 5

PREPARATION OF FTM

A gas flow consisting of 200 sccm 10% F$_2$/N$_2$ (20 sccm F$_2$) and 10.9 sccm CO was passed through the supported CsF catalyst bed described in Example 4 at an average temperature of 21° C. and at a bed pressure of 100 psig. The composition of the product gas exiting the catalyst bed was continuously monitored using an online infrared spectrometer and UV spectrometer. The composition of the product gas contained primarily FTM and N$_2$, a small amount of carbon dioxide (resulting from fluorination of residual Cs$_2$CO$_3$ on the bed), and a very small amount of F$_2$ detected (average reading was 0.53% F$_2$ before background was subtracted). From the IR, the FTM/COF$_2$ molar coefficient ratio was 82.6.

EXAMPLE 6

PREPARATION OF BDM

A gas flow consisting of 200 sccm 10% F$_2$/N$_2$ (20 sccm F$_2$) and 200 sccm CO$_2$ was passed through the supported CsF catalyst of Example 4 at an average temperature of 22° C. and at a bed pressure of 100 psig. The composition of the product gas exiting the catalyst bed was continuously monitored using an online infrared spectrometer and UV spectrometer. The composition of the product gas contained BDM, CO$_2$, and N$_2$, with very little F$_2$ detected (UV reading was 0.131, background not subtracted). From the IR, the BDM/CO$_2$ molar coefficient ratio was 0.34.

EXAMPLE 7

PREPARATION OF LOW SURFACE AREA ZIRCONIA SUPPORTED CsF CATALYST

Low surface area (less than 0.1 m$^2$/g) zirconia spheres (20.02 g of Norton Spheres, SZ-5264) were loaded into a porcelain dish and placed in a muffle furnace. The support was heated from ambient to 500° C. using a ramp of about 10° C./min ramp. The temperature was held at 500° C. for about one hour and then cooled in a desiccator. Next, 20.02 g were placed in a weighing dish and 20 ml of de-ionized water (Dl H$_2$O) was added. The material was allowed to soak for about 5 minutes and then excess surface water was removed by placing the material on a paper towel. The dried material was weighed twice; average absorption was 0.0566 g H$_2$O/g ZrO$_2$. The bulk density of this material was determined to be 1.95 g/cc.

A 585.64 g sample of dry spheres was placed in a 2-L rotary spray impregnator. A substrate solution was prepared by dissolving 160 g of Cs$_2$CO$_3$ in 66 ml of Dl H$_2$O; the final volume was 94 ml, resulting in a concentration of 1.7 g Cs$_2$CO$_3$/ml. Using a spray nozzle, 31 ml of the solution was sprayed onto the spherical ZrO$_2$ in 5–10 ml increments. The container was rolled for about 5 minutes to assure uniformity. The material was then placed in an oven at 110° C. overnight. After the specified time, the material was quickly loaded into a 2-inch o.d. quartz tube, and purged with N$_2$ until all connections were made. The tube was then purged for about 10 min at about 1 L/min flow rate with a mixture of 5% O$_2$ in He. The material was heated to 110° C. at 10° C./min, and held there for about 1 hour. The temperature was then raised to 550° C. at a rate of 5–10° C./min and held at 550° C. for about 2 hours. The material was then cooled to ambient temperature in the same O$_2$ mixture and finally purged with dry N$_2$ and packaged in moisture resistant container. The resulting supported-Cs material was shown to contain about 16.2% by weight cesium. A 476.3 g sample of the supported-Cs material was loaded into a two-ended 1-inch o.d. reactor fitted with appropriate on/off valves. The reactor was heated to 250° C. and maintained at this temperature for 24 hours with a flow of dry nitrogen (1 slpm) passing through it. After the specified time the reactor was cooled to room temperature and weighed. The weight of the supported-Cs material was 425.3 g (519 mmoles Cs). A flow of 100 sccm of 10% F$_2$ was passed through the reactor for 30 minutes at ambient temperature and then the temperature was slowly increased to 150° C. over a 4-hour period. After 625 minutes a back pressure of 25 psig was put on the reactor, and the internal temperature was maintained at 158° C. with the flow adjusted to achieve a final flow condition of 200 sccm 10% F$_2$/N$_2$. The back pressure was increased to 100 psig until the fluorination step was complete. A total of 11.4 L (472 mmoles F$_2$) was added over the two-day period.

EXAMPLE 8

PREPARATION OF BDM

The supported CsF catalyst bed prepared in Example 7 was assessed for catalytic activity in the preparation of BDM. A gas flow consisting of 200 sccm 10% F$_2$/N$_2$ (20 sccm F$_2$) and 200 sccm CO$_2$ was flowed through the supported CsF of Example 7 at an average temperature of 24° C. and at a bed pressure of 100 psig. The composition of the product gas exiting the catalyst bed was continuously monitored using an online infrared spectrometer and UV spectrometer. The product gas contained primarily BDM, CO$_2$, N$_2$, and a very small amount of F$_2$ (average reading was 0.7% F$_2$ before background was subtracted). From the IR, the BDM/CO$_2$ molar coefficient ratio was 0.453.

The activity of catalyst bed was compared to the "standard" melt-activated CsF catalyst bed described in Example 3. A gas flow consisting of 200 sccm 10% F$_2$/N$_2$(20 sccm F$_2$) and 200 sccm CO$_2$ was flowed through the "standard" CsF catalyst bed at an average temperature of 25° C. and at a bed pressure of 100 psig. The composition of the product gas exiting the catalyst bed was continuously monitored using an online infrared spectrometer and UV spectrometer. The product gas contained BDM, CO$_2$, and N$_2$, with very little F$_2$ detected (UV reading was 0.5%, background not subtracted). From the IR, the BDM/CO$_2$ molar coefficient ratio was 0.162.

The above experiments indicate that the supported CsF catalyst of this invention was unexpectedly much more active for BDM production than the "standard" CsF catalyst.

EXAMPLE 9

PREPARATION OF FTM

The supported CsF catalyst bed prepared according to the procedure of Example 8 was assessed for catalytic activity in the preparation of FTM.

A gas flow consisting of 200 sccm 10% F$_2$/N$_2$ (20 sccm F$_2$) and 7.14 sccm CO was passed through the supported CsF catalyst bed of Example 8 at an average temperature of 21° C. and at a bed pressure of 50–95 psig. The composition of the product gas exiting the catalyst bed was continuously monitored using an online infrared spectrometer and UV spectrometer. The composition of the product gas contained primarily FTM and N$_2$, a small amount of CO$_2$ (resulting from fluorination of residual Cs$_2$CO$_3$ on the bed), and a very small amount of F$_2$ detected (average reading was 0.8 % F$_2$ before background was subtracted). From the IR, the FTM/COF$_2$ molar coefficient ratio was 201.6.

EXAMPLE 10

PREPARATION OF LOW SURFACE AREA ZIRCONIA SUPPORTED CsF CATALYST

Low surface area (less than 0.1 m$^2$/g) zirconia spheres (100.05 g of Norton Spheres, SZ-5264) were loaded into a pyrex dish and placed in an oven at 228° C. for 1.5 hours. The material was then removed from the oven and placed into a dry N$_2$ purged chamber to cool. The cooled material was transferred to a weighing dish and the new weight determined; 99.94 g. The 99.94 g was returned to the pyrex dish and 100 ml of de-ionized water (Dl H$_2$O) was added. The material was allowed to soak for about 5 minutes and then excess surface water was removed by placing the material on a paper towel. The wet weight of the beads was 107.24 g. The water absorption capacity was 0.073 g H$_2$O/g ZrO$_2$. The bulk density of this material was determined to be 1.89 g/cc.

A half gallon of the ZrO$_2$ spheres was washed at room temperature and then dried at 110° C. The material was cooled in a dry N$_2$ purged chamber. Dry spheres (1.5 L) was transferred into a 6-L teflon coated rotary spray impregnator. A substrate solution was prepared by dissolving 300.06 g of CsHCO$_3$ in Dl H$_2$O to yield a total volume of 203 ml, resulting in a concentration of 1.48 g CsHCO$_3$/ml. Using a spray bottle, the 203 ml solution was sprayed onto the spherical $ZrO_2$ in 5–10 ml increments. The container was rolled for about 3 minutes at 30 rev/min. to assure uniformity. The material was then placed in an oven at 110° C. overnight. The oven temperature was ramped to 230° C. at 0.5° C./min. and hold overnight. The temperature was ramped to 250° C. and held for 4 hours. The material was placed in a dry nitrogen-purged chamber to cool. The resulting supported-Cs material was shown to contain about 7.5% by weight cesium oxide.

The supported-Cs material was converted to CsF-supported catalyst with 50% $F_2$ and subsequently shown to be effective for catalysis of the reaction between $F_2$ and $CO_2$ to produce BDM.

EXAMPLE 11

PREPARATION OF PELLETIZED $CsF/CeF_4$ CATALYST

Powdered $Cs_2CO_3$ (250 g) and $CeF_3$ (250 g) were combined in a 500 ml beaker and 25 ml of distilled water was added. The mixture was placed in a 130° C. oven for 2 hours. The mixture was then immediately extruded to ⅛ -inch extrudate. The extrudate was placed in a 160° C. oven under $N_2$ for 16 hours. The extrudate was crushed and sieved to 7–18 mesh under an inert atmosphere. The sieved material (216 g) was loaded into a 1 -inch×12-inch reactor and further dried under a 40-sccm flow of dry $N_2$ at 400° C. for 5 days. Following the specified time the reactor was cooled to 300° C. and reacted with 10.5 g of $F_2$. The $F_2$ converted the $CeF_3$ to $CeF_4$ and $Cs_2CO_3$ to CsF. The pellets retained their form during the fluorination.

EXAMPLE 12

PREPARATION OF BDM USING PELLETIZED $CsF/CeF_4$ CATALYST

A room temperature mixture of 50% $CO_2$, 40% $N_2$, and 10% $F_2$ at 100 sccm total flow was passed through the column containing the $CsF/CeF_4$ catalyst pellets at various pressures. The consumption of $F_2$ was monitored by UV spectroscopy. Data presented in Table 1 show that while the conversion of the $F_2$ was detectably higher at higher pressure, conversion was nearly complete at 40 psig. Conversion of the $F_2$ and $CO_2$ to BDM was confirmed by IR spectroscopy.

TABLE 1

Percent $F_2$ Detected Using an Ametek UV Analyzer at Various Bed Pressures of 50% $CO_2$/10% $F_2$/40% $N_2$ at 100 sccm

| Bed Pressure, psig | % $F_2$ Detected by UV* |
|---|---|
| 10 | 1.1 |
| 30 | 0.3 |
| 40 | 0.10 |
| 70 | 0.07 |

*After subtracting 0.6% due to interference by the UV absorbance of BDM.

What is claimed is:

1. An active fluoride catalyst prepared by a method comprising
    depositing on an inert support an aqueous mixture of one or more of a cerium salt and/or a cesium salt to form a supported salt;
    heating the supported salt to evaporate water, followed by heating under a dry inert gas to form a dry supported salt; and
    passing fluorine or a fluorine-containing gas over the dry supported salt to convert the salt to an active fluoride, said fluorine-containing gas selected from the group consisting of sulfur tetrafluoride, nitrogen trifluoride, xenon difluoride, krypton difluoride, oxygen difluoride, and dioxygen difluoride.

2. The active fluoride catalyst of claim 1 wherein the dry inert gas is nitrogen.

3. The active fluoride catalyst of claim 2 wherein the cerium salt and the cesium salt are selected from the group consisting of an oxide, a hydroxide, a carbonate, a bicarbonate, a chloride, a nitrate, and an acetate; and the inert support is selected from the group consisting of zirconia, alumina, titania, magnesia, a clay, an aluminosilicate, and silica.

4. The active fluoride catalyst of claim 2 wherein the salt is cesium oxide, cesium hydroxide, cesium carbonate, and/or cesium bicarbonate, and the inert support is zirconia.

5. The active fluoride catalyst of claim 2 wherein the active fluoride catalyst is in the form of particles having a surface area of at least 0.1 $m^2/g$.

6. The active fluoride catalyst of claim 2 wherein fluorine is diluted in an inert gas.

7. An active fluoride catalyst formed by a method comprising
    mixing, in an aqueous medium, a cerium salt and one or more other salt selected from the group consisting of an alkali metal salt, an alkaline earth metal salt, and another transition metal salt to form an aqueous mixture;
    heating the aqueous mixture to form a dry mixture;
    extruding the dry mixture to form an extrudate;
    heating the extrudate under a dry inert gas to form a dry extrudate;
    breaking the dry extrudate into pellets; and
    passing fluorine or a fluorine-containing gas over the pellets to form an active fluoride catalyst; said fluorine containing gas selected from the group consisting of sulfur tetrafluoride, nitrogen trifluoride, xenon difluoride, krypton difluoride, oxygen difluoride, and dioxygen difluoride.

8. The active fluoride catalyst of claim 7 wherein the dry inert gas is nitrogen.

9. The active fluoride catalyst of claim 8 wherein the cerium salt and the one or more other salt are selected from the group consisting of oxide, hydroxide, carbonate, bicarbonate, chloride, fluoride, nitrate, and acetate and the alkali metal, alkaline earth metal, and other transition metal are selected from the group consisting of cobalt, cesium, rubidium, potassium, sodium, lithium, beryllium, magnesium, calcium, strontium, and barium.

10. The active fluoride catalyst of claim 8 wherein the cerium salt is cerium trifluoride and the one or more other salt is cesium carbonate, cesium bicarbonate, cesium oxide, and/or cesium hydroxide.

11. The fluoride catalyst of claim 8 wherein the pellets have a surface area of at least about 0.1 $m^2/g$.

12. A method for making an active fluoride catalyst comprising
    depositing on an inert support an aqueous mixture of one or more of an alkali metal salt, an alkaline metal salt, and/or a transition metal salt to form a supported salt;
    heating the supported salt to evaporate water, followed by heating under a dry inert gas to form a dry supported salt; and
    passing fluorine or a fluorine-containing gas over the dry supported salt to convert the salt to an active fluoride, said fluorine-containing gas selected from the group consisting of sulfur tetrafluoride, nitrogen trifluoride, xenon difluoride, krypton difluoride, oxygen difluoride, and dioxygen difluoride.

13. The method of claim 12 wherein the dry inert gas is nitrogen.

14. The method of claim 13 wherein the alkali metal, alkaline earth metal, and transition metal are selected from the group consisting of cerium, cobalt, cesium, rubidium, potassium, sodium, lithium, beryllium, magnesium, calcium, strontium, and barium; the salt is selected from the group consisting of oxide, hydroxide, carbonate, bicarbonate, chloride, nitrate, and acetate; and the inert support is selected from the group consisting of zirconia, alumina, titania, magnesia, a clay, an aluminosilicate, and silica.

15. The method of claim 13 wherein the salt is cesium oxide, cesium hydroxide, cesium carbonate, and/or cesium bicarbonate, and the inert support is zirconia.

16. The method of claim 13 wherein the active fluoride catalyst is in the form of particles having a surface area of at least 0.1 $m^2/g$.

17. The method of claim 13 wherein fluorine is diluted in an inert gas.

18. A method of making an active fluoride catalyst formed by a method comprising mixing, in an aqueous medium, a transition metal salt with one or more other salt selected from the group consisting of an alkali metal salt, an alkaline earth metal salt, and another transition metal salt to form an aqueous mixture;

heating the aqueous mixture to form a dry mixture;

extruding the dry mixture to form an extrudate;

heating the extrudate under a dry inert gas to form a dry extrudate;

breaking the dry extrudate into pellets; and passing fluorine or a fluorine-containing gas over the pellets to form an active fluoride catalyst; said fluorine containing gas selected from the group consisting of sulfur tetrafluoride, nitrogen trifluoride, xenon difluoride, krypton difluoride, oxygen difluoride, and dioxygen difluoride.

19. The method of claim 18 wherein the dry inert gas is nitrogen.

20. The method of claim 19 wherein the transition metal salt and one or more other salt are selected from the group consisting of oxide, hydroxide, carbonate, bicarbonate, chloride, fluoride, nitrate, and acetate and the alkali metal, alkaline earth metal, and transition metal are selected from the group consisting of cerium, cobalt, cesium, rubidium, potassium, sodium, lithium, beryllium, magnesium, calcium, strontium, and barium.

21. The method of claim 19 wherein the transition metal salt is cerium trifluoride and the one or more other salt is cesium carbonate, cesium bicarbonate, cesium oxide, and/or cesium hydroxide.

* * * * *

UNITED STATES PATENT AND TRADEMARK OFFICE
CERTIFICATE OF CORRECTION

PATENT NO. : 6,524,990 B2
DATED : February 25, 2003
INVENTOR(S) : Robert George Syvret et al.

It is certified that error appears in the above-identified patent and that said Letters Patent is hereby corrected as shown below:

<u>Title page,</u>
Item [75], Inventors, delete "Frederick Carl Wilheim" and substitute therefore
-- Frederick Carl Wilhelm --

<u>Column 10,</u>
Line 56, after the first word "The" insert the word -- active --

Signed and Sealed this

Twenty-fourth Day of June, 2003

JAMES E. ROGAN
*Director of the United States Patent and Trademark Office*